(12) United States Patent
Costello et al.

(10) Patent No.: US 8,765,989 B2
(45) Date of Patent: Jul. 1, 2014

(54) PROCESS

(71) Applicant: Hoffmann-La Roche Inc., Nutley, NJ (US)

(72) Inventors: Declan Costello, Gort (IE); Gerard John Hamett, County Clare (IE); Pirmin Hidber, Seengen (CH); Ursula Hoffmann, Muttenz (CH); Thomas McCarthy, Leixlip (IE); Reinhard Reents, Muenchenstein (CH); Dennis A. Smith, County Clare (IE); Timothy Smyth, County Limerick (IE)

(73) Assignee: Hoffmann - La Roche Inc., Nutley, NJ (US)

( * ) Notice: Subject to any disclaimer, the term of this patent is extended or adjusted under 35 U.S.C. 154(b) by 0 days.

(21) Appl. No.: 13/973,129

(22) Filed: Aug. 22, 2013

(65) Prior Publication Data

US 2013/0338391 A1    Dec. 19, 2013

Related U.S. Application Data

(63) Continuation of application No. 13/681,485, filed on Nov. 20, 2012, now abandoned, which is a continuation of application No. 12/823,157, filed on Jun. 25, 2010, now abandoned.

(30) Foreign Application Priority Data

Jul. 1, 2009   (EP) ................................ 09164268

(51) Int. Cl.
*C07C 327/30*      (2006.01)

(52) U.S. Cl.
USPC ........................................................... 558/257

(58) Field of Classification Search
None
See application file for complete search history.

(56) References Cited

U.S. PATENT DOCUMENTS

| | | |
|---|---|---|
| 6,426,365 B1 | 7/2002 | Shinkai et al. |
| 6,492,370 B1 | 12/2002 | Mita et al. |

FOREIGN PATENT DOCUMENTS

| | | |
|---|---|---|
| EP | 1 072 591 | 1/2001 |
| EP | 1484317 | 8/2004 |
| JP | 2001335558 | 12/2001 |

OTHER PUBLICATIONS

Handbook for Preparation of Organic Compound Crystals—The Principle and Knowhow, Jul. 25, 2008, pp. 57-79. (Partial translation).
The Korean Office Action, issued on Aug. 16, 2013, in the related Korean application No. 2012-7002687.
Amos et al., "Reductive cleavage of aromatic disulfides using a polymer-supported phosphine reagent," J. Org. Chem., 1984, 49 (14), pp. 2637-2639.
The Japanese Office Action, issued on Jul. 30, 2013, in the related Japanese application No. 2012-518074.

*Primary Examiner* — Sun Jae Yoo

(57) ABSTRACT

The present invention relates to a process for the preparation of S-[2-[1-(2-ethylbutyl)cyclohexylcarbonylamino]-phenyl] 2-methylthiopropionate which is a useful pharmaceutical active compound.

14 Claims, No Drawings

PROCESS

PRIORITY TO RELATED APPLICATION

This application is a continuation of application of U.S. Ser. No. 13/681,485, filed on Nov. 20, 2012, which is a continuation application of U.S. Ser. No. 12/823,157 filed Jun. 25, 2010. This application claims the benefit of European Patent Application No. 09164268.6, filed Jul. 1, 2009, which is hereby incorporated by reference in its entirety.

FIELD OF THE INVENTION

The present invention relates to a process for the preparation of S-[2-[1-(2-ethylbutyl)cyclohexylcarbonylamino]-phenyl]2-methylthiopropionate, which is a useful pharmaceutically active compound.

SUMMARY OF THE INVENTION

The present invention provides a process for the preparation of S-[2-[1-(2-ethylbutyl)cyclohexylcarbonylamino]-phenyl]2-methylthiopropionate.

DETAILED DESCRIPTION OF THE INVENTION

Unless otherwise stated, the following terms used in the specification and claims have the meanings given below.

"$(C_{1-8})$alkyl" refers to a branched or straight hydrocarbon chain containing from 1 to 8 carbon atoms, such as methyl, ethyl, n-propyl, isopropyl, n-butyl, isobutyl, sec-butyl and t-butyl, pentyl, hexyl, heptyl or octyl. $(C_{1-6})$alkyl is preferred.

"$(C_{1-6})$alkoxy" means a moiety of the formula —$OR^a$, wherein $R^a$ is an $(C_{1-6})$alkyl moiety as defined herein. Examples of alkoxy moieties include, but are not limited to, methoxy, ethoxy, isopropoxy, and the like.

"Alcohol" refers to an $(C_{1-8})$alkyl as defined above substituted by an hydroxy group. Examples of alcohols include, but are not limited to, methanol, ethanol, isopropanol, propanol and butanol. Methanol is preferred.

"$(C_{3-8})$cycloalkyl" refers to a single saturated carbocyclic ring containing from 3 to 8 carbon atoms, such as cyclopropyl, cyclobutyl, cyclopentyl, cyclohexyl, cycloheptyl and cyclooctyl.

"Phenyl$(C_{1-3})$alkyl" refers to the group $R^{8ac}$—$R^{8ad}$—, wherein $R^{ac}$ and $R^{ad}$ are, respectively, "optionally substituted phenyl" and "$(C_{1-3})$alkyl" as defined above.

"Phosphine" refers to a compound of formula $PR_3$, wherein each "R" may be the same or different and is independently selected from $(C_{1-6})$alkyl, $(C_{3-6})$cycloalkyl, phenyl or phenyl$(C_{1-3})$alkyl as defined above. Representative examples include, but are not limited to, triphenylphosphine, tricyclopentylphosphine, tricylcohexylphosphine, tributylphosphine diethylphenylphosphine and tribenzylphosphine. Most preferably the phosphine is triphenylphosphine.

"Phosphinite" refers to a compound of formula $P(OR)R_2$, wherein each R may be the same or different and is independently selected from $(C_{1-6})$alkyl, $(C_{3-6})$cycloalkyl, phenyl and phenyl$(C_{1-3})$alkyl as defined above. Representative examples include, but are not limited to P,P-diphenyl-phosphinous acid phenyl ester.

"Phosphonite" refers to a compound of formula $P(OR)_2R$, wherein each R may be the same or different and is independently selected from $(C_{1-6})$alkyl, $(C_{3-6})$cycloalkyl, phenyl and phenyl$(C_{1-3})$alkyl as defined above. Representative examples include, but are not limited to P-phenyl-phosphonous acid diphenyl ester.

"Phosphite" refers to a compound of formula $P(OR)_3$, wherein each R may be the same or different and is independently selected from $(C_{1-6})$alkyl, $(C_{3-6})$cycloalkyl, phenyl and phenyl$(C_{1-3})$alkyl as defined above. Most preferably the phosphite is triisopropylphosphite.

The present invention provides a process for the preparation of S-[2-[1-(2-ethylbutyl)cyclohexylcarbonylamino]-phenyl]2-methylthiopropionate.

S-[2-[1-(2-Ethylbutyl)cyclohexylcarbonylamino]-phenyl]2-methylthiopropionate is a compound having the following formula:

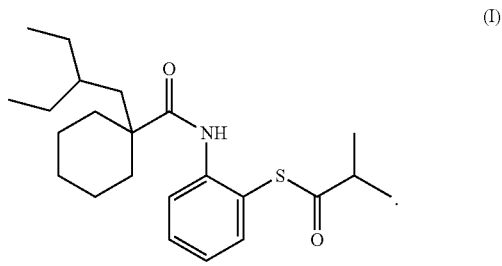 [SMILES: CCC(CC)CC1(C(=O)Nc2ccccc2SC(=O)C(C)C)CCCCC1]

(I)

The process comprises reacting a compound of formula (II),

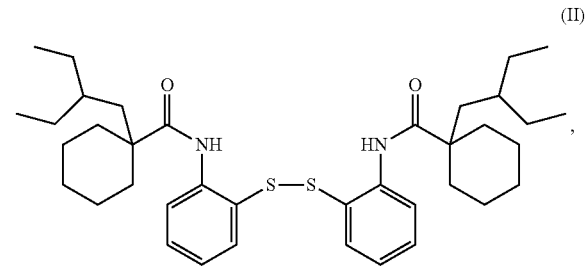 [SMILES: CCC(CC)CC1(C(=O)Nc2ccccc2SSc2ccccc2NC(=O)C2(CC(CC)CC)CCCCC2)CCCCC1]

(II)

with isobutyric anhydride and a reducing agent. Such a reaction is an acylation reaction.

In an embodiment of the invention, the reducing agent is selected from the group consisting of: phosphines, phosphinites, phosphonites and phosphites.

In an embodiment of the invention, the reducing agent is a phosphine.

In an embodiment, the reducing agent is selected from the group consisting of: triisopropylphosphite, triphenylphosphine and tributylphosphine.

In an embodiment of the invention, the reducing agent is triphenylphosphine or tributylphosphine.

In an embodiment, the reducing agent is triphenylphosphine.

In an embodiment, at least 0.10 M of the reducing agent is used in the reaction.

In an embodiment of the invention, excess reducing agent is oxidized with an oxidizing agent.

In an embodiment of the invention, the oxidizing agent is potassium peroxymonosulfate or hydrogen peroxide.

In an embodiment of the invention, the oxidizing agent is hydrogen peroxide.

In embodiments in which the reducing agent is a phosphine, the acylation reaction produces a phosphine oxide. In embodiments in which the reducing agent is a phosphinite, the reaction produces a phosphinate. In embodiments in which the reducing agent is a phosphonite, the reaction produces a phosphonate. In embodiments in which the reducing agent is a phosphite, the reaction produces a phosphate.

In an embodiment wherein the reducing agent is a phosphine, a phosphinite, a phosphonite or a phosphite, the acylation reaction is followed by the removal of the respective phosphine oxide, phosphinate, phosphonate or phosphate with water/alcohol extraction from an organic solvent.

Unless otherwise stated, the organic solvent used for reactions referred to herein may be an ether-like solvent (e.g. tetrahydrofuran, methyltetrahydrofuran, diisopropyl ether, t-butylmethyl ether or dibutyl ether, dimethyl acetal or dioxane), an ester-like solvent (e.g. ethyl acetate, butyl acetate), an aliphatic hydrocarbon solvent (e.g. hexane, heptane or pentane), a saturated alicyclic hydrocarbon solvent (e.g. cyclohexane or cyclopentane), an aromatic solvent (e.g. toluene or t-butyl-benzene), a nitrile (e.g. acetonitrile), an amide (e.g. dimethylformamide, N-methylpyrrolidine), a chlorinated solvent (e.g. dichloromethane), or dimethyl sulfoxide.

In an embodiment, the solvent for reactions is heptane or toluene.

Unless otherwise stated, the organic solvent used for extractions referred herein may be an ether-like solvent (e.g. methyltetrahydrofuran, diisopropyl ether, t-butylmethyl ether or dibutyl ether, dimethyl acetal or dioxane), an ester-like solvent (e.g. ethyl acetate, butyl acetate), an aliphatic hydrocarbon solvent (e.g. hexane, heptane or pentane), a saturated alicyclic hydrocarbon solvent (e.g. cyclohexane or cyclopentane), or an aromatic solvent (e.g. toluene or t-butyl-benzene).

In an embodiment, the solvent for extractions is heptane.

The compound of formula (II) can be prepared according to scheme 1.

Scheme 1

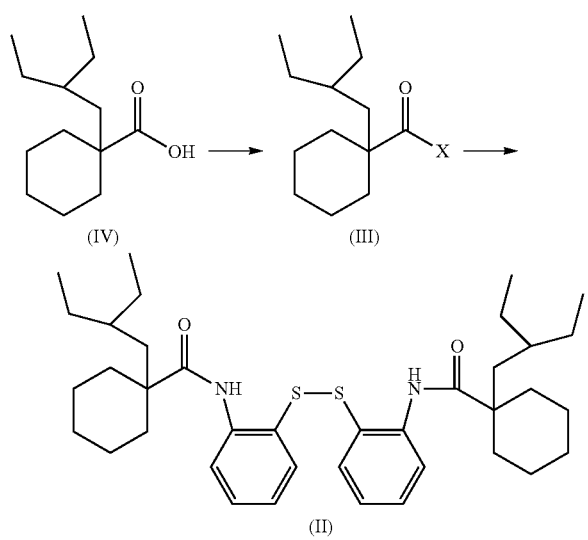

In the above scheme, X is I, Br, Cl or F. In particular, the process comprises reacting a cyclohexanecarboxylic acid derivative of formula (IV) with a halogenating agent, such as $PX_3$, $PX_5$, $SOX_2$ or NCX, to obtain the acyl halide of formula (III). The halogenating step is preferably carried out in the presence of tri-$(C_1$-$C_5)$alkylamine. Furthermore, the process comprises reacting the compound of formula (III) with bis(2-aminophenyl)disulfide to acylate the amino groups of the bis(2-aminophenyl)disulfide in the presence of a base (e.g. N-methylmorpholine, di-N-methylpiperazine, pyridine), thus producing the compound of formula (II).

In an embodiment, the halogenating agent is chosen from the group consisting of: thionyl chloride, phosphorus pentachloride, oxalyl chloride, phosgene, diphosgene, triphosgene, phosphorus tribromide, cyanuric fluoride, and cyanuric chloride.

In an embodiment, the halogenating agent is thionyl chloride or phosgene.

In an embodiment of the invention, the compound formula (III) is one wherein X is Cl.

Furthermore the invention may comprise the step of crystallizing S-[2-[1-(2-ethylbutyl)cyclohexylcarbonylamino]-phenyl]2-methylthiopropionate.

S-[2-[1-(2-Ethylbutyl)cyclohexylcarbonylamino]-phenyl]2-methylthiopropionate can be crystallized by a combined cooling and solvent-anti-solvent process. The solvent and anti-solvent should be miscible. Both addition modes—anti-solvent to S-[2-[1-(2-ethylbutyl)cyclohexylcarbonylamino]-phenyl]2-methylthiopropionate solution (preferred) or 5-[2-[1-(2-ethylbutyl)cyclohexylcarbonylamino]-phenyl]2-methylthiopropionate solution to anti-solvent—are possible. With water as the anti-solvent, the solvent should be a water-miscible solvent. Examples of such solvents include but are not restricted to acetone, ethanol, isopropanol, propanol, and mixtures thereof.

In an embodiment, S-[2-[1-(2-ethylbutyl)cyclohexylcarbonylamino]-phenyl]2-methylthiopropionate is crystallized from ethanol (solvent) and water (anti-solvent).

For the crystallization, S-[2-[1-(2-ethylbutyl)cyclohexylcarbonylamino]-phenyl]2-methylthiopropionate is dissolved at elevated temperature in ethanol (preferably between 40° C. and 70° C.) and cooled until supersaturation is achieved (preferably to room temperature). S-[2-[1-(2-Ethylbutyl)cyclohexylcarbonylamino]-phenyl]2-methylthiopropionate seed crystals are added, preferably as a suspension in ethanol/water 1:1 (m/m). After seeding, the suspension is aged for an appropriate time (preferably 60 minutes). Subsequently, and while stirring, water is added until the desired ethanol to water ratio is achieved (preferentially ethanol:water=7:3 (m/m)). After complete addition, the crystallization mixture is stirred for about 30 min, cooled to the final temperature (preferentially −10° C.) and further aged at the same temperature. The crystals are isolated by filtration and washed with a mixture of ethanol-water (preferably ethanol:water 3:1 (m/m). Subsequently, the wet crystals are dried, most preferably at 40° C., under reduced pressure until the weight is constant Alternatively, the mode of addition can be changed. The hot solution of S-[2-[1-(2-ethylbutyl)cyclohexylcarbonylamino]-phenyl]2-methylthiopropionatein ethanol is added to the water phase preferably containing S-[2-[1-(2-ethylbutyl)cyclohexylcarbonylamino]-phenyl]2-methylthiopropionate seed crystals. In this case, the ethanol:water ratio can be smaller than 7:3 (m/m), preferably 6:4 (m/m) or even smaller. The suspension is further processed as described above.

S-[2-[1-(2-Ethylbutyl)cyclohexylcarbonylamino]-phenyl]2-methylthiopropionate can also be crystallized by cooling a solution of S-[2-[1-(2-ethylbutyl)cyclohexylcarbonylamino]-phenyl]2-methylthiopropionate in a non-polar solvent such as hexane(s), cyclohexane, heptane, or pentane. Most preferably, S-[2-[1-(2-ethylbutyl)cyclohexylcarbonylamino]-phenyl]2-methylthiopropionate is crystallized from heptane.

In another embodiment, the process of the present invention further comprises the following steps:
a) forming a solution of S-[2-[1-(2-ethylbutyl)cyclohexylcarbonylamino]-phenyl]2-methylthiopropionate in acetone, ethanol, isopropanol or propanol at a temperature of 40° C. to 70° C.;
b) cooling the solution until supersaturation, preferably to room temperature; (wherein supersaturation is well understood by the person skilled in the art, see J. W. Mullin, "Crystallization", fourth edition, Butterworth-Heinemann, 2001, ISBN 0 7506 4833 3, pages 123-131);
c) adding seed crystals of S-[2-[1-(2-ethylbutyl)cyclohexylcarbonylamino]-phenyl]2-methylthiopropionate;
d) optionally aging the suspension, preferably for at least 10 min, most preferably for 60 minutes;
e) adding water while stirring until the desired solvent/water ratio is obtained, preferably the solvent/water ratio is between 9:1 and 1 to 9, more preferably 8:2 and 2:8 most preferably 7:3 (m/m);
f) optionally further stirring the mixture;
g) cooling the mixture to a temperature below 0° C., more preferably between 0° C. and −20° C., most preferably to −10° C., to effect the crystallization and precipitation of S-[2-[1-(2-ethylbutyl)cyclohexylcarbonylamino]-phenyl] 2-methylthiopropionate from the solution thereof,
h) separating the crystalline S-[2-[1-(2-ethylbutyl)cyclohexylcarbonylamino]-phenyl]2-methylthiopropionate from the liquid component of the mixture, preferably the crystalline S-[2-[1-(2-ethylbutyl)cyclohexylcarbonylamino]-phenyl]2-methylthiopropionate is filtered out.

In an embodiment, the invention relates to a crystalline form of the compound of formula (I) as produced using the above process.

The starting materials and reagents which do not have their synthetic route explicitly disclosed herein are generally available from commercial sources or are readily prepared using methods well known to the person skilled in the art. For instance, the compound of formula (IV) can be prepared according to the procedures described in Shinkai et al., J. Med. Chem. 43:3566-3572 (2000), WO 2007/051714 or WO 2008/074677.

In general, the nomenclature used in this Application is based on AUTONOM™ 2000, a Beilstein Institute computerized system for the generation of IUPAC systematic nomenclature. Chemical structures shown herein were prepared using MDL ISIS™ version 2.5 SP2. Any open valency appearing on a carbon, oxygen or nitrogen atom in the structures herein indicates the presence of a hydrogen atom.

EXAMPLES

The following examples are provided for the purpose of further illustration and are not intended to limit the scope of the claimed invention.

The following abbreviations and definitions are used: Ar (argon); acid chloride (1-(2-ethyl-butyl)-cyclohexanecarbonyl chloride); amidodisulfide (N,N'-(dithiodi-2,1-phenylene)bis[1-(2-ethylbutyl)-cyclohexanecarboxamide]); amidothiophenol (1-(2-ethylbutyl)-N-(2-mercaptophenyl)-cyclohexanecarboxamide); thioester (S-[2-[1-(2-ethylbutyl) cyclohexanecarbonylamino]-phenyl]2-methylthiopropionate); DTDA (2,2'-dithiodianiline); eq. (equivalent); g (gram); EtOH (ethanol); IPC (in process control); GC (gas chromatography); h (hour); M (Molarity [moles/L]); MeOH (methanol); ml (milliliter); NMM(N-methylmorpholine); RT (room temperature); TBP (tributylphosphine); TEP (triethylphosphite); TPP (triphenylphosphine), TPPO (triphenylphosphine oxide), methylthioether (1-(2-ethylbutyl)-N-[2-(methylthio)phenyl]-cyclohexanecarboxamide), ethylthioether (1-(2-ethylbutyl)-N-[2-(ethylthio)phenyl]-cyclohexanecarboxamide, isopropylthioether (1-(2-ethylbutyl)-N-[2-(isopropylthio)phenyl]-cyclohexanecarboxamide.

Example 1

Use of Triphenylphosphine in Toluene at Reflux

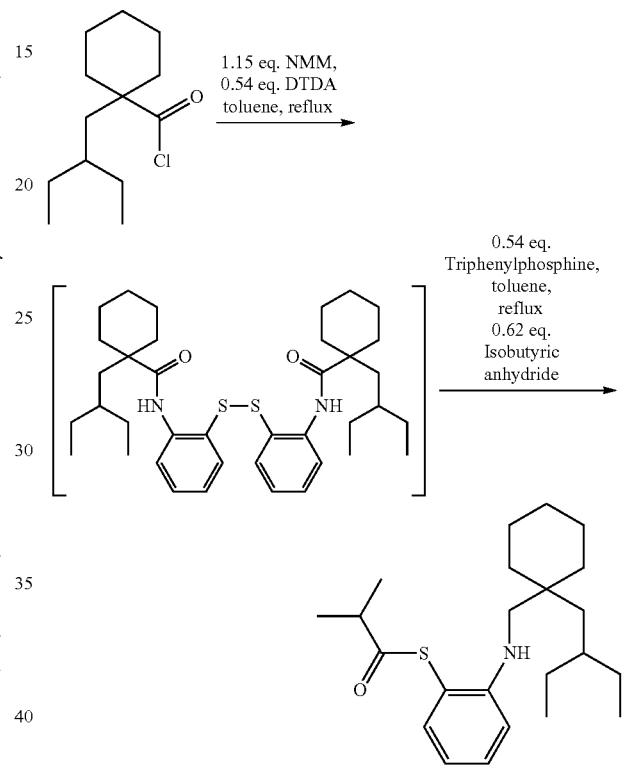

In a double jacket vessel under argon 13.4 g DTDA (54 mmol, 0.54 eq) was suspended in 65 g toluene (75 ml). 11.6 g NMM (115 mmol, 1.15 eq) was added. The dark brown suspension was heated to 100° C. and the suspension became a clear solution. 24.5 g acid chloride (100 mmol, 1.0 eq, Assay: 94.2 (% mass)) was added to this solution over a period of 30 minutes at 100° C. The reaction mixture was heated at reflux (115° C.) and then stirred for 7 h under reflux.

The reaction mixture was cooled to RT and extracted with 20 g water twice. The toluene phase was completely evaporated at 50° C. under reduced pressure. To the residue was added 59 g toluene (68 ml).

14.2 g of TPP (54 mmol, 0.54 eq) was dissolved in 36 g toluene (42 ml) followed by the addition of the above amidodisulfide solution in toluene at 25° C. 9.82 g isobutyric anhydride (62 mmol, 0.621 eq) was added and rinsed with 9 g toluene (10 ml). The reaction mixture was heated to reflux (115° C.) and then stirred for 6 h under reflux. An IPC-sample showed 38.6% TPPO, 0% amidothiophenol, 0% amidodisulfide and 61.0% thioester.

The reaction mixture was completely evaporated at 50° C. under reduced pressure. To the residue was added 109 g heptane (160 ml). The solution was warmed to 40° C. and extracted four times with each a mixture of 89 g MeOH (112 ml) and 48 g water (48 ml). The phases were allowed to separate for 10 minutes after each extraction. The aqueous phases were discarded.

The thioester heptane solution was completely evaporated at 50° C. under reduced pressure. To the oily residue was added 117 g EtOH (148 ml) and the suspension was heated at 50° C. until the solution was clear. A lab filter unit with external heating (50° C.) was charged with an activated charcoal filter pad.

The reddish-brown thioester solution in ethanol was filtered at 50° C. through the above filter unit within approx. 20 minutes and became light brown. The flask and the filter unit were washed with 16 g EtOH (20 ml). The solution was filtered through a polishing filter (Millipore®) at 50° C. into an Erlenmeyer flask. The flask and the filter unit were rinsed with 16 g EtOH (20 ml). Obtained were ca. 170 g EtOH-solution (assay thioester 19.8%, 87.8% yield)

The filtered thioester EtOH solution was transferred into the double jacket vessel at 50° C. The flask was rinsed with 16 g EtOH (20 ml).

The clear solution was cooled to RT and seeded with a suspension of thioester (0.3 mmol, 0.003 eq) seeding crystals in 2.0 g EtOH/water 1:1 (m/m) (2.3 ml). The seeded solution was stirred until a well mixed suspension was obtained (60 minutes), and then, while stirring, water was added with the use of a Dosimat® (Metrohm® automatic dispenser) within 60 minutes at RT. After complete addition the crystallization mixture was stirred for 30 minutes and then cooled to −10° C. ($T_i$) within 3.5 h and further stirred for min. 60 minutes at this temperature. The suspension was isolated by filtration on paper and the isolated crystals were washed with a mixture of 36 g EtOH (45 ml) and 15 g water (cooled to −10° C.). The wet crystals (approx. 45 g) were dried at 45° C. under reduced pressure for 16 h until the weight was constant. 32.9 g thioester (83.9 mmol, yield 83.9%) were obtained.

Example 2

Use of Tributylphosphine in Toluene at Reflux

In a double jacket vessel under argon 13.4 g DTDA (54 mmol, 0.54 eq) was suspended in 65 g toluene (75 ml). 11.6 g NMM (115 mmol, 1.15 eq) was added. The dark brown suspension was heated to 100° C. and the suspension became a clear solution. 23.9 g acid chloride (100 mmol, 1.0 eq, Assay: 96.7 (% mass)) was added to this solution over a period of 30 minutes at 100° C. The reaction mixture was heated to reflux (115° C.) and then stirred for 6 h under reflux.

The reaction mixture was cooled to RT and washed with 20 g water twice. The toluene phase was completely evaporated at 50° C. under reduced pressure. To the residue was added 59 g toluene (68 ml).

The above toluene solution was transferred into another vessel and rinsed with 17 g toluene (20 ml). To this toluene solution was added at room temperature via dropping funnel 9.81 g isobutyric anhydride (62 mmol, 0.62 eq). The dropping funnel was rinsed with 9 g (10 ml) toluene. Subsequently 11.5 g TBP (54 mmol, 0.54 eq.) was added via dropping funnel within 25 minutes at RT. The dropping funnel was rinsed with 10 g (12 ml) toluene. After 3 hours additional 0.08 g isobutyric anhydride (0.5 mmol, 0.005 eq) was added and the reaction mixture was stirred for another 90 minutes. An IPC-sample showed 0.52% amidothiophenol, 0% amidodisulfide and 90.8% thioester.

The reaction mixture was completely evaporated at 40-85° C. under reduced pressure. To the residue was added 109 g heptane (160 ml). The heptane solution was washed at room temperature four times with each a mixture of 89 g MeOH (112 ml) and 48 g water (48 ml). The phases were allowed to separate for 10 minutes after each extraction. The aqueous phases were discarded.

The thioester heptane solution was completely evaporated at 45-60° C. under reduced pressure. To the oily residue was added 117 g EtOH (148 ml) and the suspension was heated at 50° C. until the solution was clear. A lab filter unit with external heating (50° C.) was charged with an activated charcoal filter pad and a 0.45 µm membrane (Millipore®) filter.

The reddish-brown thioester EtOH solution was filtered at 50° C. through above filter unit within approx. 20 minutes and became light brown. The flask and the filter unit were washed with 32 g EtOH (40 ml). Obtained were 180 g EtOH-solution (containing 18.8% thioester, 86.9% yield)

The filtered thioester EtOH solution was transferred into the double jacket vessel at 50° C. The flask was rinsed with 16 g EtOH (20 ml).

The clear solution was cooled to RT and seeded with a suspension of thioester (0.3 mmol, 0.003 eq.) seeding crystals in 2.0 g EtOH/water 1:1 (m/m) (2.3 ml). The seeded solution was stirred until a well mixed suspension was obtained (60 minutes), and then, while stirring, 72 g water was added with the use of a Dosimat® (Metrohm automatic dispenser) within 60 minutes at RT. After complete addition the crystallization mixture was stirred for 30 minutes and then cooled to −10° C. ($T_i$) with a ramp of 10° C./h and further stirred for 60 minutes at this temperature. The suspension was isolated by filtration on paper and the isolated crystals were washed with a mixture of 36 g EtOH (45 ml) and 15 g water (cooled to −10° C.). The wet crystals (40.7 g) were dried at 45° C. under reduced pressure for 16 h until the weight was constant. 33.0 g thioester (assay 99.1%, 83.8 mmol, yield 83.8%) were obtained.

Example 3

Use of Triethylphosphite (TEP) in Toluene at Reflux

In a double jacket vessel under argon 13.4 g DTDA (54 mmol, 0.54 eq) was suspended in 65 g toluene (75 ml). 11.6 g NMM (115 mmol, 1.15 eq) was added. The dark brown suspension was heated to 100° C. and the suspension became a clear solution. 23.9 g acid chloride (100 mmol, 1.0 eq, Assay: 96.7 (% mass)) was added to this solution over a period of 30 minutes at 100° C. The reaction mixture was heated to reflux (115° C.) and then stirred for 6 h under reflux.

The reaction mixture was cooled to RT and washed twice with 20 g water twice. The toluene phase was completely evaporated at 50° C. under reduced pressure. To the residue was added 59 g toluene (68 ml).

The above toluene solution was transferred into another vessel and rinsed with 17 g toluene (20 ml). To the toluene solution was added at room temperature via dropping funnel 9.81 g isobutyric anhydride (62 mmol, 0.62 eq). The dropping funnel was rinsed with 17 g (20 ml) toluene. Subsequently 9.16 g TEP (54 mmol, 0.54 eq.) was added via dropping funnel within 25 minutes at RT. The dropping funnel was rinsed with 10 g (12 ml) toluene. The reaction mixture was heated to 60° C. and stirred for 20 minutes at this temperature. An IPC-sample showed 0% amidothiophenol, 0% amidodisulfide, 87.9% thioester and 5.0% ethylthioether.

The reaction mixture was completely evaporated at 40-85° C. under reduced pressure. To the residue was added 109 g heptane (160 ml). The heptane solution was washed at room temperature four times with each a mixture of 89 g MeOH (112 ml) and 48 g water (48 ml). The phases were allowed to separate for 10 minutes after each extraction. The aqueous phases were discarded.

The thioester heptane solution was completely evaporated at 45-60° C. under reduced pressure. To the oily residue was added 117 g EtOH (148 ml) and the suspension was heated at 50° C. until the solution was clear. A lab filter unit with external heating (50° C.) was charged with an activated charcoal filter pad and a 0.45 µm membrane (Millipore®) filter.

The reddish-brown thioester EtOH solution was filtered at 50° C. through above filter unit within approx. 20 minutes and became light brown. The flask and the filter unit were washed with 32 g EtOH (40 ml).

The filtered thioester EtOH solution was transferred into the double jacket vessel at 50° C. The flask was rinsed with 16 g EtOH (20 ml).

The clear solution was cooled to RT and seeded with a suspension of thioester (0.3 mmol, 0.003 eq.) seeding crystals in 2.0 g EtOH/water 1:1 (m/m) (2.3 ml). The seeded solution was stirred until a well mixed suspension was obtained (60 minutes), and then, while stirring, 72 g water was added with the use of a Dosimat® (Metrohm automatic dispenser) within 60 minutes at RT. After complete addition the crystallization mixture was stirred for 30 minutes and then cooled to –10° C. ($T_i$) with a ramp of 10° C./h and further stirred for 60 minutes at this temperature. The suspension was isolated by filtration on paper and the isolated crystals were washed with a mixture of 36 g EtOH (45 ml) and 15 g water (cooled to –10° C.). The wet crystals (38.6 g) were dried at 45° C. under reduced pressure for 16 h until the weight was constant. 33.2 g thioester (assay 99.5%, 84.4 mmol, yield 84.4%) were obtained. 0.48% of ethylthioether was observed.

Example 4

Use of TEP in Toluene Under Reflux

In a double jacket vessel under argon 13.4 g DTDA (54 mmol, 0.54 eq) was suspended in 65 g toluene (75 ml). 11.6 g NMM (115 mmol, 1.15 eq) was added. The dark brown suspension was heated to 100° C. and the suspension became a clear solution. 23.9 g acid chloride (100 mmol, 1.0 eq, Assay: 96.7 (% mass)) was added to this solution over a period of 30 minutes at 100° C. The reaction mixture was heated at reflux (115° C.) and then stirred for 6 h under reflux.

The reaction mixture was cooled to RT and washed twice with each 20 g water. The toluene phase was completely evaporated at 50° C. under reduced pressure. To the residue was added 59 g toluene (68 ml).

The above toluene solution was transferred into another vessel and rinsed with 17 g toluene (20 ml). To the toluene solution was added at room temperature via dropping funnel 9.81 g isobutyric anhydride (62 mmol, 0.62 eq). The dropping funnel was rinsed with 17 g (20 ml) toluene. Subsequently 9.16 g TEP (54 mmol, 0.54 eq.) were added via dropping funnel within 20 minutes at 24-30° C. The dropping funnel was rinsed with 10 g (12 ml) toluene. The reaction mixture was heated to 30° C. and stirred for 30 minutes at that temperature. An IPC-sample showed 0% amidothiophenol, 0% amidodisulfide, 87.6% thioester and 5.2% ethylthioether The toluene solution was washed at room temperature 5 times with each 100 g water (100 ml). The phases were always allowed to separate for 5 minutes. The aqueous phases were discarded.

The thioester toluene solution was completely evaporated at 45-60° C. under reduced pressure. To the oily residue was added 117 g EtOH (148 ml) and the suspension was heated at 50° C. until the solution was clear. A lab filter unit with external heating (50° C.) was charged with an activated charcoal filter pad and a 0.45 µm membrane (Millipore®) filter.

The reddish-brown thioester EtOH solution was filtered at 50° C. through above filter unit within approx. 20 minutes and became light brown. The flask and the filter unit were washed with 32 g EtOH (40 ml).

The filtered thioester EtOH solution was transferred into the double jacket vessel at 50° C. The flask was rinsed with 16 g EtOH (20 ml).

The clear solution was cooled to RT and seeded with a suspension of thioester (0.3 mmol, 0.003 eq.) seeding crystals in 2.0 g EtOH/water 1:1 (m/m) (2.3 ml). The seeded solution was stirred until a well mixed suspension was obtained (60 minutes), and then while stirring 72 g water was added with the use of a Dosimat® (Metrohm® automatic dispenser) within 60 minutes at RT. After complete addition the crystallization mixture was stirred for 30 minutes and then cooled to –10° C. ($T_i$) with a ramp of 10° C./h and further stirred for 60 minutes at this temperature. The suspension was isolated by filtration on paper and the isolated crystals were washed twice with each a mixture of 36 g EtOH (45 ml) and 15 g water (cooled to –10° C.). The wet crystals (43.9 g) were dried at 45° C. under reduced pressure for 16 h until the weight was constant. 33.1 g thioester (assay 99.5%, 84.5 mmol, yield 84.5%) were obtained. 0.41% of ethylthioether was observed.

Example 5

With Triethylphosphite (Reaction at –20° C.), No Triethylphosphate Extraction

In a double jacket vessel under argon 13.4 g DTDA (54 mmol, 0.54 eq) was suspended in 65 g toluene (75 ml). 11.6 g NMM (115 mmol, 1.15 eq) was added. The dark brown suspension was heated to 100° C. and the suspension became a clear solution. 24.1 g acid chloride (100 mmol, 1.0 eq, Assay: 95.8 (% mass)) was added to this solution over a period of 30 minutes at 100° C. The reaction mixture was heated at reflux (115° C.) and then stirred for 6 h under reflux.

The reaction mixture was cooled to RT and washed twice with each 20 g water. The toluene phase was completely evaporated at 50° C. under reduced pressure. To the residue was added 59 g toluene (68 ml).

The above toluene solution was transferred into another vessel and rinsed with 17 g toluene (20 ml). To the toluene solution was added at room temperature via dropping funnel 9.82 g isobutyric anhydride (62 mmol, 0.62 eq). The dropping funnel is rinsed with 28 g (32 ml) toluene. Subsequently the reaction mixture was cooled to –20° C. $T_i$ and 9.16 g TEP (54 mmol, 0.54 eq.) were added via syringe pump within 60 minutes at –20° C. $T_i$. The reaction mixture was stirred for 60 minutes. An IPC-sample showed 2.1% amidothiophenol, 0% amidodisulfide, 93.4% thioester and 2.1% ethylthioether.

The reaction mixture was completely evaporated at 45-60° C. under reduced pressure. To the oily residue was added 117 g ethanol (148 ml) and the suspension was heated at 50° C. until the solution was clear. A lab filter unit with external heating (50° C.) was charged with an activated charcoal filter pad and a 0.45 µm membrane (Millipore®) filter.

The reddish-brown thioester ethanol solution was filtered at 50° C. through above filter unit within approx. 20 minutes and became light brown. The flask and the filter unit were washed with 32 g ethanol (40 ml).

The filtered thioester ethanol solution was transferred into the double jacket vessel at 50° C. The flask was rinsed with 16 g ethanol (20 ml).

The clear solution was cooled to 20° C. and seeded with a suspension of thioester (0.3 mmol, 0.003 eq.) seeding crystals in 2.0 g ethanol/water 1:1 (m/m) (2.3 ml). The seeded solution was stirred until a well mixed suspension was obtained (60 minutes), and then, while stirring 72 g water was added with the use of a Dosimat® (Metrohm® automatic dispenser) within 60 minutes at 20-24° C. After complete addition the crystallization mixture was stirred for 30 minutes and then cooled to −10° C. ($T_i$) with a ramp of 10° C./h and further stirred overnight at this temperature. The suspension was isolated by filtration on paper and the isolated crystals were washed twice with each a mixture of 36 g ethanol (45 ml) and 15 g water (cooled to −10° C.). The wet crystals (43.7 g) were dried at 45° C. under reduced pressure for 6 h until the weight was constant. 34.1 g thioester (assay 98.7%, 86.4 mmol, yield 86.3%) were obtained. 0.32% of ethylthioether was observed.

Example 6

Use of Triisopropylphosphite (TIP) at 0° C., No Triisopropylphosphate Extraction In a double jacket vessel under argon 13.4 g DTDA (54 mmol, 0.54 eq) was suspended in 65 g toluene (75 ml). 11.6 g N-methyl morpholine (115 mmol, 1.15 eq) was added. The dark brown suspension was heated to 100° C. and the suspension became a clear solution. 24.1 g acid chloride (100 mmol, 1.0 eq, Assay: 95.9 (% mass)) was added to this solution over a period of 30 minutes at 100° C. The reaction mixture was heated at reflux (115° C.) and then stirred for 6 h under reflux.

The reaction mixture was cooled to 25° C. and washed twice with each 20 g water. The toluene phase was completely evaporated at 50° C. under reduced pressure. To the residue was added 59 g toluene (68 ml).

The above toluene solution was transferred into another vessel and rinsed with 17 g toluene (20 ml). To the toluene solution was added at room temperature via dropping funnel 9.82 g isobutyric anhydride (62 mmol, 0.62 eq). The dropping funnel was rinsed with 28 g (32 ml) toluene. Subsequently the reaction mixture was cooled to −2 to 0° C. $T_i$ and 11.84 g triisopropylphosphite (54 mmol, 0.54 eq.) were added via syringe pump within 60 minutes at 0° C. $T_i$. The reaction mixture was stirred for 30 minutes. An IPC-sample showed <0.1% amidothiophenol, 0.17% amidodisulfide, 95.7% thioester and 1.6% isopropylthioether.

The reaction mixture was completely evaporated at 45-60° C. under reduced pressure. To the oily residue was added 117 g ethanol (148 ml) and the suspension was heated at 50° C. until the solution was clear. A lab filter unit with external heating (50° C.) was charged with an activated charcoal filter pad and a 0.45 μm membrane (Millipore®) filter.

The reddish-brown thioester ethanol solution was filtered at 50° C. through above filter unit within approx. 20 minutes and became light brown. The flask and the filter unit were washed with 32 g ethanol (40 ml).

The filtered thioester ethanol solution was transferred into the double jacket vessel at 50° C. The flask was rinsed with 16 g ethanol (20 ml).

The clear solution was cooled to 20° C. and seeded with a suspension of thioester (0.3 mmol, 0.003 eq.) seeding crystals in 2.0 g ethanol/water 1:1 (m/m) (2.3 ml). The seeded solution was stirred until a well mixed suspension was obtained (60 minutes), and then, while stirring 72 g water was added with the use of a Dosimat® (Metrohm® automatic dispenser) within 60 minutes at 20-24° C. After complete addition the crystallization mixture was stirred for 30 minutes and then cooled to −10° C. ($T_i$) with a ramp of 10° C./h and further stirred overnight at this temperature. The suspension was isolated by filtration on paper and the isolated crystals were washed twice with each a mixture of 36 g ethanol (45 ml) and 15 g water (cooled to −10° C.). The wet crystals (55.1 g) were dried at 45° C. under reduced pressure over the weekend. 34.7 g thioester (assay 99.5%, 88.6 mmol, yield 88.6%) were obtained. 0.10% of isopropylthioether was observed.

Example 7

Pretreatment of Quenched Amidodisulfide Reaction Mixture with Isobutyric Anhydride at 80° C. Before Reduction with TIP In a double jacket vessel under argon 4.0 g DTDA (16.2 mmol, 0.54 eq) was suspended in 19.5 g toluene (22.5 ml). 3.49 g N-methyl morpholine (34.5 mmol, 1.15 eq) was added. The dark brown suspension was heated to 100° C. and the suspension became a clear solution. 7.15 g acid chloride (30 mmol, 1.0 eq, Assay: 96.8 (% mass)) was added to this solution over a period of 30 minutes at 100° C. The reaction mixture was heated at reflux (115° C.) and then stirred for 6 h under reflux.

The reaction mixture was cooled to 25° C. and washed twice with each 6 g water. The toluene phase was completely evaporated at 50° C. under reduced pressure. To the residue was added 17.7 g toluene (20.4 ml).

The above toluene solution was transferred into another vessel and rinsed with 11.8 g toluene (13.6 ml). To the toluene solution was added at room temperature 3.08 g isobutyric anhydride (19.5 mmol, 0.65 eq). The reaction mixture was stirred for 60 minutes at 20° C., 60 minutes at 50° C. and 3 hours 30 minutes at 80° C. Subsequently the reaction mixture was cooled to 10° C. $T_i$ and 3.2 g triisopropylphosphite (14.6 mmol, 0.49 eq.) were added via syringe pump within 60 minutes at 10° C. $T_i$. The reaction mixture was stirred for 90 minutes, after which additional 377 mg triisopropylphosphite were added. After further 3 hours of stirring, an IPC-sample showed 0% amidothiophenol, 0% amidodisulfide, 90.4% thioester and 0.36% isopropylthioether.

Example 8

Use of TPP in Dichloromethane at Room Temperature

In a double jacket vessel under argon 31.0 g DTDA (125 mmol, 0.54 eq) is suspended in 146 g toluene. 26.9 g NMM (266 mmol, 1.15 eq) was added. The dark brown suspension was heated to 100° C. and the suspension became a clear solution. 54.9 g acid chloride (232 mmol, 1.0 eq, Assay: 97.3 (% mass)) was added to this solution over a period of 30 minutes at 100° C. The reaction mixture was heated at reflux (115° C.) and then stirred for 7 h under reflux.

The reaction mixture was cooled to RT and extracted twice with each 45 g water. The toluene phase was completely evaporated at 50° C. under reduced pressure. To the residue was added 180 g methylene chloride).

32.8 g of TPP (125 mmol, 0.54 eq) was dissolved in 111 g dichloromethane followed by the addition of the above amidodisulfide solution in dichloromethane at 25° C. 22.8 g isobutyric anhydride (144 mmol, 0.621 eq) were added and rinsed with 29 g dichloromethane. The reaction mixture was stirred at room temperature for 36 h (results after 2 hours: 4.3% amidothiophenol, <0.1% amidodisulfide; results after 36 hours: 1.7% amidothiophenol, <0.1% amidodisulfide).

The reaction mixture was completely evaporated at 50° C. under reduced pressure. To the residue was added 224 g heptane. The solution was warmed to 40° C. and extracted 4 times with a mixture of 199 g MeOH and 110 g water. The phases were always allowed to separate for 10 minutes. The aqueous phases were discarded.

The thioester heptane solution was completely evaporated at 50° C. under reduced pressure. To the oily residue was added 262 g EtOH and the suspension was heated at 50° C. until the solution was clear. A lab filter unit with external heating (50° C.) was charged with an activated charcoal filter pad.

The reddish-brown thioester EtOH solution was filtered at 50° C. through above filter unit within approx. 20 minutes and became light brown. The flask and the filter unit were washed with 34 g EtOH. The solution was filtered over a polishing (Millipore®) filter at 50° C. into an Erlenmeyer flask.

The filtered thioester EtOH solution was transferred into the double jacket vessel at 50° C. The flask was rinsed with 34 g EtOH.

The clear solution was cooled to RT and seeded with a suspension of 262 mg thioester seeding crystals in 4.4 g EtOH/water 1:1 (m/m). The seeded solution was stirred until a well mixed suspension was obtained (60 minutes), and then, while stirring 160 g water was added with the use of a Dosimat® (Metrohm® automatic dispenser) within 60 minutes at RT. After complete addition the crystallization mixture was stirred for 30 minutes and then cooled to $-10°$ C. ($T_i$) within 3.5 h and further stirred for min. 60 minutes at this temperature. The suspension was isolated by filtration on paper and the isolated crystals are washed with a mixture of 80 g EtOH and 34 g water (cooled to $-10°$ C.). The wet crystals (approx. 98 g) are dried at 40° C. under reduced pressure for 16 h until the weight was constant. 78.8 g thioester (assay 97.1%, yield 83.7%, 0.4% amidothiophenol) are obtained.

Example 9

Use of TPP in Toluene at Room Temperature

In a double jacket vessel under argon 31.0 g DTDA (125 mmol, 0.54 eq) was suspended in 146 g toluene. 26.9 g NMM (266 mmol, 1.15 eq) was added. The dark brown suspension was heated to 100° C. and the suspension became a clear solution. 54.9 g acid chloride (232 mmol, 1.0 eq, Assay: 97.3 (% mass)) was added to this solution over a period of 30 minutes at 100° C. The reaction mixture was heated at reflux (115° C.) and then stirred for 7 h under reflux.

The reaction mixture was cooled to RT and extracted twice with each 45 g water. The toluene phase was completely evaporated at 50° C. under reduced pressure. To the residue was added 132 g toluene).

32.8 g of TPP (125 mmol, 0.54 eq) was dissolved in 80 g toluene followed by the addition of the above amidodisulfide solution in toluene at 25° C. 22.8 g isobutyric anhydride (144 mmol, 0.621 eq) are added and rinsed with 20 g toluene. The reaction mixture was stirred at room temperature for 24 h (results after 3 hours: 10.6% amidothiophenol, <0.1% amidodisulfide; results after 24 hours: 4.9% amidothiophenol, <0.1% amidodisulfide).

The reaction mixture was completely evaporated at 50° C. under reduced pressure. To the residue was added 224 g heptane. The solution was warmed to 40° C. and extracted 4 times with a mixture of 199 g MeOH and 110 g water. The phases are always allowed to separate for 10 minutes. The aqueous phases are discarded.

The thioester heptane solution was completely evaporated at 50° C. under reduced pressure. To the oily residue was added 262 g EtOH and the suspension was heated at 50° C. until the solution was clear. A lab filter unit with external heating (50° C.) was charged with an activated charcoal filter pad.

The reddish-brown thioester EtOH solution was filtered at 50° C. through above filter unit within approx. 20 minutes and became light brown. The flask and the filter unit are washed with 34 g EtOH. The solution was filtered over a polishing (Millipore®) filter at 50° C. into an Erlenmeyer flask.

The filtered thioester EtOH solution was transferred into the double jacket vessel at 50° C. The flask was rinsed with 34 g EtOH.

The clear solution was cooled to RT and seeded with a suspension of 262 mg thioester seeding crystals in 4.4 g EtOH/water 1:1 (m/m). The seeded solution was stirred until a well mixed suspension was obtained (60 minutes), and then, while stirring 160 g water was added with the use of a Dosimat® (metrohm automatic dispenser) within 60 minutes at RT. After complete addition the crystallization mixture was stirred for 30 minutes and then cooled to $-10°$ C. ($T_i$) within 3.5 h and further stirred for min. 60 minutes at this temperature. The suspension was isolated by filtration on paper and the isolated crystals are washed with a mixture of 80 g EtOH and 34 g water (cooled to $-10°$ C.). The wet crystals (approx. 119 g) are dried at 40° C. under reduced pressure for 16 h until the weight was constant. 81 g thioester (assay 98.4%, yield 88.2%, 1.0% amidothiophenol) are obtained.

Example 10

Use of Excess TPP in Toluene Followed by $H_2O_2$ Oxidation

In a double jacket vessel under argon 13.5 g DTDA (54 mmol, 0.54 eq) was suspended in 65 g toluene (75 ml). 11.6 g N-methylmorpholine (115 mmol, 1.15 eq) was added. The dark brown suspension was heated to 100° C. and the suspension becomes a clear solution. 23.7 g acid chloride (100 mmol, 1.0 eq, assay: 97.3% (% mass)) was added to this solution over a period of 30 minutes at 100° C. The reaction mixture was heated to reflux (115° C.) and then stirred for 5 h under reflux.

The reaction mixture was cooled to 25° C. and extracted twice with each 20 g water. The toluene phase was completely evaporated at 50° C. under reduced pressure. To the residue was added 59 g toluene (68 ml).

14.7 g Triphenylphosphine (56 mmol, 0.56 eq) was dissolved in 36 g toluene (42 ml) and the above amidodisulfide solution in toluene was added at 25° C. 9.82 g isobutyric anhydride (62 mmol, 0.621 eq) was added and rinsed with 9 g toluene (10 ml). The reaction mixture was heated to reflux (115° C.) and then stirred for 5 h under reflux. An IPC-sample showed 36.7% TPPO, 0.16% amidothiophenol, 0% amidodisulfide and 60.2% thioester.

The reaction mixture was completely evaporated at 50° C. under reduced pressure. To the residue was added 109 g heptane (160 ml). The suspension was warmed to 25-30° C. and a mixture of 89 g methanol (112 ml) and 48 g water (48 ml) was added. 3.4 g $H_2O_2$ (10% solution in water) (10 mmol, 0.10 eq.) was added and the biphasic mixture was stirred for 30 minutes. The aqueous phase was removed and the organic phase was extracted three times with each a mixture of 89 g methanol (112 ml) and 48 g water (48 ml). The phases were allowed to separate for 10 minutes after each extraction. The aqueous phases were discarded.

The thioester solution was completely evaporated at 50° C. under reduced pressure. To the oily residue was added 117 g ethanol (148 ml) and the suspension was heated at 50° C. until the solution was clear. A lab filter unit with external heating (50° C.) was charged with an activated charcoal filter pad.

The reddish-brown thioester solution was filtered at 50° C. through above filter unit within approx. 20 minutes and became light brown. The flask and the filter unit were washed with 16 g ethanol (20 ml). The solution was filtered through a polishing filter at 50° C. into an Erlenmeyer flask. The flask and the filter unit was rinsed with 16 g ethanol (20 ml).

The filtered thioester ethanol solution was transferred into the double jacket vessel at 50° C. The flask was rinsed with 16 g ethanol (20 ml).

The clear solution was cooled to 20° C. and seeded with a suspension of thioester (0.3 mmol, 0.003 eq) seeding crystals in 2.0 g ethanol/water 1:1 (m/m) (2.3 ml). The seeded solution was stirred until a well mixed suspension was obtained (60 minutes), then, while stirring, water was added with the use of a Dosimat® within 60 minutes at 24° C. After complete addition the crystallization mixture was stirred for 30 minutes and then cooled to −10° C. ($T_i$) within 3.5 h and further stirred for 60 minutes at this temperature. The suspension was isolated by filtration on paper and the isolated crystals were washed with a mixture of 36 g ethanol (45 ml) and 15 g water (cooled to −10° C.). The wet crystals (approx. 45 g) were dried at 45° C. under reduced pressure for 16 h until the weight was constant. 34.0 g thioester (assay 99.7%, 87 mmol, yield 87.0%) were obtained.

Example 11

Use of Excess TPP in Heptane Followed by $H_2O_2$ Oxidation

In a double jacket vessel under argon 13.4 g 2,2'-dithio dianiline (54 mmol, 0.54 eq) was suspended in 51 g heptane (75 ml). 11.6 g N-methyl morpholine (115 mmol, 1.15 eq) was added. The dark brown suspension was heated to 100° C. and the suspension became a clear solution. 23.7 g CAT-acid chloride (CAT13) (100 mmol, 1.0 eq, Assay: 97.3 (% mass)) was added to this solution over a period of 30 minutes at 100° C. The reaction mixture was heated to 113° C. under pressure (max 2 bar) and then stirred for 7 h at this temperature.

The reaction mixture was cooled to 25° C. and extracted twice with each 20 g water. The heptane phase was heated to reflux at normal pressure and azeotroped using a Dean-Stark-trap until the heptane phase was dry. The heptane phase was cooled to room temperature.

14.7 g triphenyl phosphine (56 mmol, 0.56 eq) and 24 g heptane (35 ml) were charged to the above solution in heptane at 25° C. 9.82 g isobutyric anhydride (62 mmol, 0.621 eq) were added and rinsed with 7 g heptane (10 ml). The reaction mixture was heated at reflux (100° C.) and then stirred for 5 h under reflux. An IPC-sample showed 10.8% TPPO, 0% amidothiophenol, 0% amidodisulfide and 84.3% thioester.

The reaction mixture was cooled to 35° C. and diluted with 27 g heptane (40 ml) and a mixture of 89 g methanol (112 ml) and 37 g water. 11.3 g of 3% $H_2O_2$-solution (10 mmol, 0.10 eq.) were added and the biphasic mixture was stirred for 30 minutes at 35° C. The aqueous phase is separated and the organic phase was extracted 4 times with each a mixture of 89 g methanol (112 ml) and 48 g water (48 ml). The phases were always allowed to separate for 10 minutes. The aqueous phases were discarded.

The thioester heptane solution was completely evaporated at 50° C. under reduced pressure. To the oily residue was added 117 g ethanol (148 ml) and the suspension is heated at 50° C. until the solution was clear. A lab filter unit with external heating (50° C.) was charged with an activated charcoal filter pad.

The reddish-brown thioester ethanol solution was filtered at 50° C. through above filter unit within approx. 20 minutes and becomes light brown. The flask and the filter unit were washed with 16 g ethanol (20 ml). The solution was filtered over a polish filter at 50° C. into an Erlenmeyer flask. The flask and the filter unit was rinsed with 16 g ethanol (20 ml).

The filtered thioester ethanol solution was transferred into the double jacket vessel at 50° C. The flask was rinsed with 16 g ethanol (20 ml).

The clear solution was cooled to 18-20° C. and seeded with a suspension of thioester (0.3 mmol, 0.003 eq) seeding crystals in 2.0 g ethanol/water 1:1 (m/m) (2.3 ml). The suspension was stirred until a well mixed suspension is obtained (60 minutes), subsequently and while stirring water was added with the use of a Dosimat® within 60 minutes at 24° C. After complete addition the crystallization mixture was stirred for 30 minutes and then cooled to −10° C. ($T_i$) within 3.5 h and further stirred for min. 60 minutes at this temperature. The suspension was isolated by filtration on paper and the isolated crystals were washed with a mixture of 36 g ethanol (45 ml) and 15 g water (cooled to −10° C.). The wet crystals (42.5 g) were dried at 45° C. under reduced pressure for 16 h until the weight was constant. 34.6 g of thioester (88.9 mmol, yield 88.9%) were obtained.

Example 12

Extraction of TPPO with a Multi Stage Centrifugal Extractor (Model Used LX526 from Rousselet & Robatel)

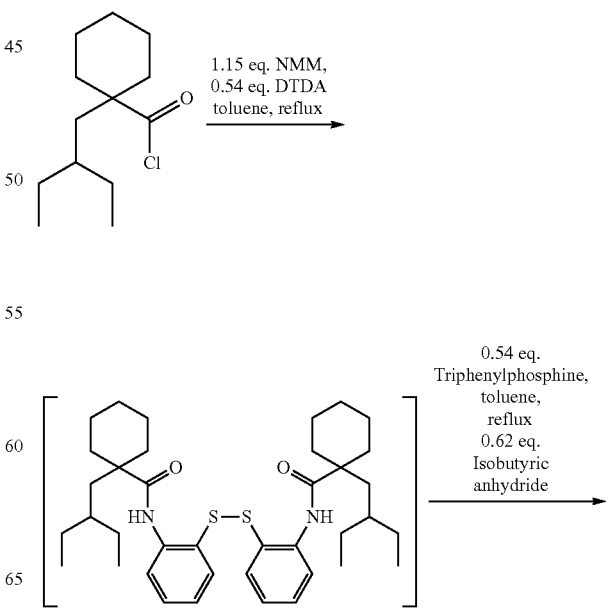

-continued

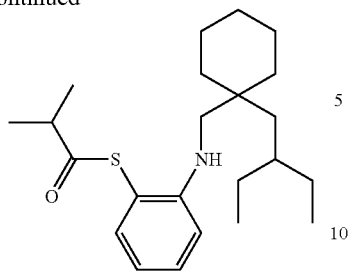

In a double jacket vessel 114 kg DTDA (459 mol, 0.54 eq) and 99 kg NMM (979 mol, 1.15 eq) was suspended in 555 kg toluene (640 l). The suspension was heated to 100° C. and the suspension became a clear solution. 197 kg acid chloride (854 mol, 1.0 eq, assay corrected) was added to this solution over a period of 30 minutes at 100° C. The reaction mixture was heated at reflux (115° C.) and then stirred for 6 hours under reflux.

The reaction mixture was transferred to another double jacket vessel and rinsed with 43 kg toluene (49 l). The reaction mixture was cooled to RT and extracted with 171 kg water twice. 100 kg solvent was evaporated at 50° C. under reduced pressure. At constant volume 500 kg toluene (434 l) was added to the residue while evaporating solvent.

121 kg of TPP (461 mol, 0.54 eq) was dissolved in 282 kg toluene (325 l) followed by the addition of the above amidodisulfide solution in toluene at 25° C. 84 kg isobutyric anhydride (531 mol, 0.62 eq) was added. The reaction mixture was heated to reflux (115° C.) and then stirred for 6 hours under reflux.

The reaction mixture was completely evaporated at 50° C. under reduced pressure. To the residue was added 930 kg heptane (1348 l). The solution was warmed to 40° C. and extracted with a mixture of 181 kg MeOH (229 l) and 98 kg water (98 l). The aqueous phase was discarded.

The heptane solution (feed 1200 l/h) was extracted at 40° C. with methanol/water (65/35) (feed 800 l/h) via a 6 stage centrifugal extractor at 1800 rpm. The vessel was rinsed with 104 kg heptane (150 l) and the heptane was extracted against methanol/water (65/35) in the extractor under the same conditions.

The thioester heptane solution was completely evaporated at 55° C. under reduced pressure. To the oily residue was added 1258 kg EtOH (1593 l) and the suspension was heated at 50° C. until the solution was clear. A 16" filter unit with external heating (50° C.) was charged with three activated charcoal filter modules.

The reddish-brown thioester solution in ethanol was filtered at 50° C. through the above filter unit and an additional polishing filter (5 μm) within approx. 2 hours and became yellowish. The vessel and the filters were rinsed with 156 kg EtOH (198 l).

The clear solution was cooled to RT and seeded with a suspension of 1 kg thioester (2.6 mol, 0.003 eq) seeding crystals in 17 kg EtOH/water 1:1 (m/m). The seeded solution was stirred until a well mixed suspension was obtained (60 minutes), and then, while stirring, 615 kg water (615 l) was added within 60 minutes at RT. After complete addition the crystallization mixture was stirred for 30 minutes and then cooled to −10° C. (T$_i$) within 3.5 hours and further stirred for min. 60 minutes at this temperature.

The suspension was separated on a centrifuge and the isolated crystals were washed with a mixture of 307 kg EtOH (390 l) and 128 kg water (cooled to −10° C.).

The wet crystals (approx. 378 kg) were dried in a spherical dryer at 45° C. under reduced pressure for 11 hours. 298.8 kg thioester (assay 99.5%, 763 mol, yield 89.3%) were obtained.

The invention claimed is:

1. A process for the preparation of the compound of formula (I),

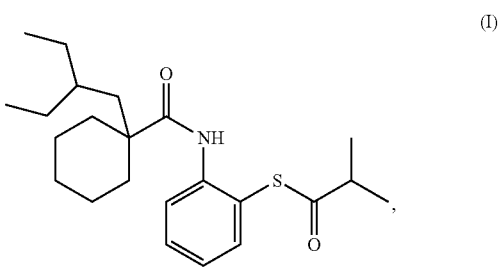

which comprises reacting a compound of formula (II),

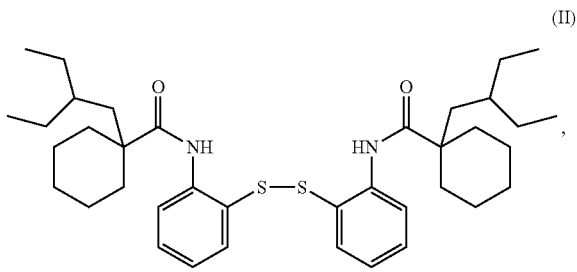 [SMILES: CCC(CC)CC1(C(=O)Nc2ccccc2SSc2ccccc2NC(=O)C2(CC(CC)CC)CCCCC2)CCCCC1]

with isobutyric anhydride and a reducing agent.

2. A process according to claim 1, wherein said reaction is carried out with at least 0.10 M of said reducing agent.

3. A process according to claim 1, wherein the said reducing agent is selected from the group consisting of: phosphines, phosphinites, phosphonites and phosphites.

4. A process according to claim 1, which further comprises the oxidation of excess reducing agent with an oxidizing agent.

5. A process according to claim 4, wherein the oxidizing agent is peroxymonosulfate or hydrogen peroxide.

6. A process according to claim 1, wherein the said reducing agent is a phosphine.

7. A process according to claim 1, wherein the said reducing agent is triphenyl phosphine.

8. A process according to claim 3 which further comprises the removal of the phosphine oxide, phosphinate, phosphonate or phosphate produced in said reaction using water/alcohol extraction from an organic solvent.

9. A process according to claim 8, wherein said reducing agent is a phosphine and the phosphine oxide produced in said reaction is removed using water/alcohol extraction from an organic solvent.

10. A process according to claim 1 which further comprises crystallizing the compound of formula (I) using a solvent-antisolvent process with water as the antisolvent and the solvent being a water-miscible solvent.

11. A process according to 10 wherein the water miscible solvent is acetone, ethanol, isopropanol, propanol or mixtures thereof.

12. A process according to claim 1 which further comprises crystallizing the compound of formula (I) by cooling a solution of said compound of formula (I) in a non-polar solvent.

13. A process according to claim 1, which further comprises the following steps:
   a) forming a solution of said compound of formula (I) in acetone, ethanol, isopropanol or propanol at a temperature of 40° C. to 70° C.;
   b) cooling the solution until supersaturation;
   c) adding seed crystals of the compound of formula (I);
   d) optionally aging the suspension;
   e) adding water while stirring until the desired solvent/water ratio is obtained;
   f) optionally further stirring the mixture;
   g) cooling the mixture to a temperature below 0° C. to effect the crystallization and precipitation of the compound of formula (I) from the solution thereof, and
   h) separating the crystalline compound of formula (I) from the liquid component of the mixture.

14. A process according to claim 4, wherein the oxidizing agent is hydrogen peroxide.

\* \* \* \* \*